United States Patent [19]

Ramnaney

[11] Patent Number: 4,738,804
[45] Date of Patent: Apr. 19, 1988

[54] MANUFACTURE OF OIL SOLUBLE POLYVALENT METAL SULFONATES

[76] Inventor: Ashok Ramnaney, 16522 Debra La., Cerritos, Calif. 90701

[21] Appl. No.: 766,134

[22] Filed: Aug. 15, 1985

[51] Int. Cl.$^4$ ............................................. C07C 143/24
[52] U.S. Cl. .................................................. 260/505 P
[58] Field of Search .......................... 260/504 S, 505 P

[56] References Cited

U.S. PATENT DOCUMENTS

| | | | |
|---|---|---|---|
| 1,487,240 | 3/1924 | Higgins et al. | 260/504 S |
| 2,453,690 | 11/1948 | Bray . | |
| 2,616,936 | 11/1952 | Mammen et al. . | |
| 2,689,221 | 9/1954 | Bray . | |
| 2,732,344 | 1/1956 | Bray . | |
| 2,746,987 | 5/1957 | Bray . | |
| 2,815,370 | 12/1957 | Hutchings et al. . | |
| 2,820,056 | 1/1958 | Gerhart et al. | 260/505 P |
| 2,824,126 | 2/1958 | Bray . | |
| 3,033,898 | 5/1962 | Bray . | |
| 3,225,086 | 12/1965 | Sias et al. | 260/504 S |
| 4,144,266 | 3/1979 | Plummer et al. . | |
| 4,177,208 | 12/1979 | Aristide et al. . | |
| 4,240,978 | 12/1980 | Berg . | |
| 4,269,789 | 5/1981 | Zornes . | |
| 4,361,520 | 11/1982 | Luetnelechwab . | |

FOREIGN PATENT DOCUMENTS 822816 11/1959 United Kingdom .

Primary Examiner—Alan Siegel
Attorney, Agent, or Firm—Poms, Smith, Lande & Rose

[57] ABSTRACT

An improved method for the direct production and recovery of oil soluble polyvalent metal sulfonates of petroleum hydrocarbons is provided wherein a hydrocarbon feed stock is sulfonated and mixed with water and a hydrocarbon solvent to form a top layer and a bottom sludge layer containing undesirable water soluble sulfonic acids and ions. The top layer is treated with a partition breaking solvent causing it to separate into three phases, a top oil phase, a middle phase containing most of the desired oil soluble sulfonic acids and a lower brine phase containing undesirable water soluble sulfonic acids and ions. The middle phase is directly treated with an oxide or hydroxide of a polyvalent metal without a prior neutralization step to produce neutral oil soluble polyvalent metal sulfonate which can readily be recovered from solution.

16 Claims, 1 Drawing Sheet

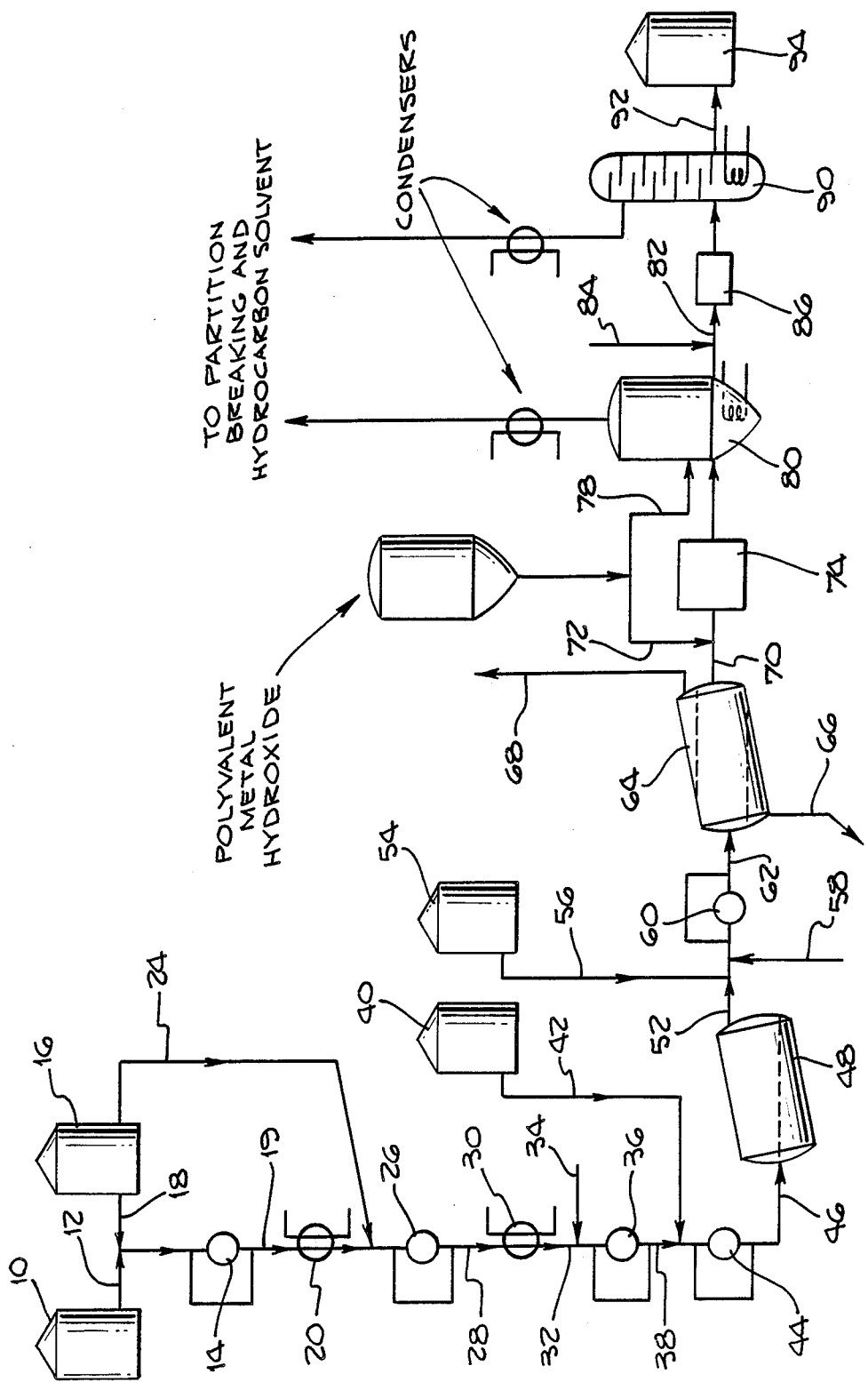

MANUFACTURE OF OIL SOLUBLE POLYVALENT METAL SULFONATES

FIELD OF THE INVENTION

The present invention relates in a broad aspect to an improved method for the production of oil soluble polyvalent metal sulfonates. More particularly, the present invention is directed to an improved method for the direct manufacture and recovery of oil soluble polyvalent metal mahogany sulfonates of petroleum hydrocarbons from natural or refined feedstocks.

BACKGROUND OF THE INVENTION

The production and recovery of petroleum sulfonates is well-known in the art. Typically, a hydrocarbon feed stock such as natural or refined petroleum oil is treated with a sulfonating agent such as fuming sulfuric acid, sulfur trioxide or oleum (sulfur trioxide dissolved in sulfuric acid). This treatment produces oil soluble sulfonic acids, commonly known as "mahogany acids" and water soluble sulfonic acids, commonly known as "green acids" as well as a number of other by-products including unused acid, sulfates, sulfites, and acid sludge. Additional byproducts include unreacted hydrocarbon oil which is commonly known as "white oil."

In the majority of the prior art sulfonation processes, the desired oil soluble sulfonates are recovered by washing the treated hydrocarbon feed stock with ammonia or caustic soda (sodium hydroxide) to neutralize the oil soluble sulfonic acids and then extracting the sodium sulfonates so produced with a solvent such as water, alcohol, low molecular weight hydrocarbons, or mixtures of these compounds.

The extracted sodium sulfonate can then be converted into polyvalent metal sulfonates such as calcium, barium, or other metal sulfonate by treatment of the sodium sulfonate with the appropriate salt. Such conversion usually takes place after purification to remove residual inorganic salt and green acid sulfonates. For example, treatment of the sodium sulfonate with excess calcium chloride will produce calcium sulfonate and sodium chloride. The sodium chloride can then be removed with the excess calcium chloride though residual chloride ion will remain with the metal sulfonate.

Attempts to avoid this two-step neutralization and conversion process by the direct neutralization of sulfonic acid with calcium chloride have been unsuccessful because of the formation of troublesome calcium sulfate slime and because of the difficulty of separating undesirable water soluble green acid sulfonates from oil soluble sulfonates when both are in the form of their calcium soaps.

One method of reducing the amount of green sulfonic acid is to reduce the relative proportion of paraffinic or long-chain hydrocarbon molecules in the petroleum feed stock because the oil soluble sulfonic acids are produced from the sulfonation of the aromatic portion of hydrocarbon feed stocks. Other methods rely on the previously described neutralization and two-phase hydrocarbon solvent and water extraction technique followed by conversion to the desired polyvalent metal sulfonate form. While the polyvalent metal salts of mahogany sulfonic acid are oil soluble and almost entirely insoluble in water, the readily water soluble polyvalent metal salts of green sulfonic acid are partially oil soluble when in the presence of oil soluble acid salts. Because the oil soluble polyvalent metal sulfonates are often used as detergent and rust preventative additives to lubricating oils, the presence of water soluble green sulfonic acid is objectionable in lubricating applications where moisture may be encountered. Even a relatively small proportion of water soluble sulfonate may result in excessive water corrosion of lubricated metal components.

Accordingly, because of the complexity and attendant expense associated with these prior art methods for the production and recovery of oil soluble polyvalent metal sulfonates, it is a principal object of the present invention to provide a method for the direct production and recovery of oil soluble polyvalent metal sulfonates without the use of a preliminary sodium hydroxide or ammonia neutralization step.

It is an additional object of the present invention to provide a method for the direct production of oil soluble polyvalent metal sulfonates which are free from water soluble sulfonates or that contain water soluble sulfonates in insignificant proportions so that the polyvalent metal sulfonates are suitable for use in compound lubricants.

It is a further object of the present invention to disclose a method for the production of oil soluble polyvalent metal sulfonates having only negligible levels of chloride ions, sulfate ions and sulfite ions.

It is a further object of the present invention to provide a method for the production and recovery of oil soluble polyvalent metal sulfonates in which the sulfonates can be readily recovered through filtration without the need for diatomaceous earth.

SUMMARY OF THE INVENTION

The present invention achieves these and other objects by providing a process for the direct production and recovery of oil soluble polyvalent metal sulfonates from sulfonated hydrocarbon feed stock. The polyvalent metal sulfonates produced in accordance with the method of the present invention are readily filterable, contain negligible amounts of chloride ions, sulfate and sulfite ions, and insignificant amounts of water soluble green sulfonates. Moreover, the method of the present invention does not utilize a preliminary caustic or ammonia neutralization step and produces oil soluble polyvalent metal sulfonates directly from the oil soluble sulfonic acids of the treated hydrocarbon feed stock.

In a broad aspect the method of the present invention comprises the following steps. First, a hydrocarbon feed stock, preferably having an aromatic hydrocarbon content of from 5 percent to 95 percent, is treated with a sulfonating agent. Suitable sulfonating agents include concentrated sulfuric acid, sulfur trioxide, and oleum. The reaction mixture so produced is mixed with water to quench the sulfonation reaction and to release the desirable oil soluble sulfonic acid which is held in solution by the concentrated sulfuric acid phase. Next, a hydrocarbon solvent such as napththa is added to the mixture to promote the formation and separation of an acid sludge layer containing most of the undesirable green sulfonic acids, unused sulfuric acid, sulfate and sulfite ions, which settles and separates from an upper layer of unreacted oil and desirable oil soluble sulfonic acids as well as trace quantities of green sulfonic acids, sulfate and sulfite ions.

After removal of the acid sludge, which can be discarded or recycled, the upper oil and solvent layer is mixed with a partition breaking solvent such as butyl alcohol or aqueous butyl alcohol which promotes the separation and formation of the mixture into three phases or layers. The upper phase is comprised mainly of unreacted hydrocarbon oil and a slight amount of oil soluble sulfonic acid. The lower or brine phase contains oil insoluble, water soluble green sulfonic acids, sulfate ions and sulfite ions. The middle phase contains the desired oil soluble, water insoluble sulfonic acid.

Next, the bottom brine phase may be drawn off and neutralized with any base forming salt and water and may be discarded after recovering the hydrocarbon solvent and partition breaking solvent contained therein. Similarly, the top phase containing unreacted oil can be drawn off and stripped of solvents and then utilized as lubricating oil or for other purposes.

By virtue of this three-phase separation, the remaining middle layer comprises purified oil soluble sulfonic acid, hydrocarbon solvent and partition breaking solvent. It is then treated with an oxide or hydroxide of a polyvalent metal such as calcium, magnesium, barium or strontium or other alkali-earth metal. Excess polyvalent metal oxide or hydroxide can be removed easily from the treated solution through filtration, straining, or centrifugation. The polyvalent metal sulfonate so formed can be readily recovered from the solution through stripping the solvents therefrom.

It will be appreciated that the neutral oil soluble polyvalent metal sulfonates so produced have been purified of sulfate and sulfite ions in the three-phase separation procedure. What is more, because it was not necessary to convert the monovalent metal mahogany sulfonate to the polyvalent form with an appropriate water soluble polyvalent metal salt such as calcium chloride, the neutral polyvalent metal mahogany sulfonates produced by the method of the present invention are free of chloride ions. Further, by eliminating the preliminary neutralization step of the prior art the present invention eliminates the need to utilize monovalent metal salts such as sodium hydroxide and thereby eliminates the expense associated with this aspect of the prior art processes.

BRIEF DESCRIPTION OF THE DRAWING

FIG. 1 is a schematic representation of the process of the present invention.

DETAILED DESCRIPTION OF A PREFERRED EMBODIMENT

The method of the present invention is applicable to a variety of hydrocarbon feed stocks. Preferably, crude oil which has been solvent refined to remove polynuclear aromatic hydrocarbons and resins will be utilized. Additionally, a mild sulfuric acid treatment on the order of 10 to 50 pounds of 90 to 98 percent sulfuric acid per barrel of crude can be used instead of or in conjunction with solvent refining. Refined residual oils such as "bright stock" which have been deresined may also be used. Similarly, oils made by the alkylation of benzene with long hydrocarbon side chains and high alkylates produced as byproducts in household detergent manufacturing can also be employed in the present invention. Petroleum oils containing substantial amounts of aromatic compounds, naphthenic compounds or unsaturated compounds are also useful in the method of the present invention as are petroleum oil stocks prepared by mixing such compounds.

In that it is the aromatic portion of the feed stock which is converted to the desirable oil soluble sulfonic acids, it is preferred that the hydrocarbon feed stock contain on the order of 5 percent to 95 percent aromatic compounds. A preferred hydrocarbon feed stock would contain approximately 25 percent to 75 percent by weight aromatic compounds.

In many instances the petroleum feed stocks useful as starting materials in the method of the present invention will have a viscosity range on the order of 300 SSU to 600 SSU at 100 degrees F. and an API gravity ranging from approximately 5 degrees to 60 degrees at 60 degrees F., although higher viscosity feed stocks may be employed.

Typical boiling ranges for suitable feed stocks are on the order of 100 degrees F. to 1400 degrees F. Also, it is preferred that the aromatic components of the hydrocarbon feed stock have molecular weights ranging from 200 to 1000 with preferred feed stocks having aromatic molecules whose molecular weight ranges from approximately 300 to 600.

Referring more particularly to the drawing of FIG. 1, the method of the present invention is as follows. First, the hydrocarbon feed stock is conducted from a suitable source, such as storage tank 10 via line 12 to mixer 14 where it is intimately mixed with a stream of sulfonating agent supplied from tank 16 via line 18. The sulfonating agent can be any sulfonating agent known in the art such as concentrated sulfuric acid, sulfur trioxide, or oleum. Mixer 14 can be any efficient mixing machine known in the art such as a high-speed centrifugal pump or gear-type pump.

The treated hydrocarbon feed stock is then conducted by line 19 to a condenser 20 where the temperature of the treated feed stock is controlled to a desired temperature below approximately 130 degrees F.

It will be appreciated that improved results can be obtained by mixing the hydrocarbon feed stock with the sulfonating agent and cooling in stages. Thus, as shown in the preferred embodiment illustrated by FIG. 1, the reaction mixture is conducted from condenser 20 through line 22 to a second mixer 26. An additional sulfonating agent from tank 16 is mixed with the cooled reaction mixture from condensor 20 via line 24. Additional mixing and sulfonation of the hydrocarbon feed stock reaction mixture is provided by mixer 26 before the mixture is directed through line 28 to a second condensor 30 where the temperature of the reaction mixture is again controlled to the desired temperature range.

After leaving condensor 30 via line 32 the sulfonation reaction is quenched through the addition of water to the reaction mixture via line 34. Preferably, approximately 1 to 3 percent water is added to the reaction mixture by weight. In addition to quenching the sulfonation reaction, the water also serves to release the desired oil soluble sulfonic acids which would normally be held in solution by the highly concentrated sulfuric acid of the sulfonating agent. Additional mixing is provided by mixer 36 after the addition of water. However, it will be appreciated that while it is preferred to mix the sulfonating agent in stages as shown in FIG. 1, the provision of a second condensor 30 and second mixer 26 is not necessary to practice the method of the present invention.

After mixing with water and exiting mixer 36 via line 38, a hydrocarbon solvent from tank 40 is added to the reaction mixture via line 42. Suitable hydrocarbon solvents include aromatic solvents such as benzene, toulene, xylene, or petroleum naphta, preferably having a boiling point in the range of 160 degrees F. to 350 degrees F. to aid in their subsequent removal from solution. The hydrocarbon solvent is intimately mixed with the quenched reaction mixture by mixer 44 before being conducted by line 46 to settling tank 48. The hydrocarbon solvent promotes the formation of an acid sludge layer containing the majority of the undesirable water soluble green sulfonic acids as well as unused sulfuric acid, sulfate ions, and sulfite ions.

The reaction mixture and hydrocarbon solvent is allowed to stand in settler 48 for a sufficient period of time in which to form two separate layers, the previously described lower acid sludge layer and an upper layer generally comprising unreacted hydrocarbon oil, oil soluble sulfonic acid, as well as hydrocarbon solvent and a relatively small amount of water soluble sulfonic acid, sulfate ions and sulfite ions. A typical residence time within settler 48 would be on the order of twenty-four hours at room temperature. However, other residence times and temperatures may be utilized to practice the method of the present invention where appropriate to those skilled in the art.

After settling, the lower sludge layer is drawn off from settler 48 through line 50 and either discarded or treated to recover any sulfuric acid and hydrocarbons contained therein. It should be noted that in some circumstances three layers will form in settler 48. In this situation, the bottom two layers containing the acid sludge, unreacted acid and water soluble sulfonic acids are removed.

The upper layer formed in settler 48 is drawn off by line 52 and mixed with a partition breaking liquid or solvent conducted from tank 54 through line 56. Preferred partition breaking solvents are any of a variety of oil soluble, partially water soluble organic liquids consisting of carbon, hydrogen and oxygen and having a sufficiently low boiling point to facilitate their later removal and recovery from the reaction mixture of the instant invention. Additionally, it is preferred that the partition breaking solvents utilized have a sufficiently low viscosity so as not to disturb the various phases of the process.

Preferred partition breaking solvents contain from 4–8 carbon molocules which provides a boiling point significantly below the decomposition temperature of the desired polyvalent metal sulfonate to enable the partition breaking solvent to be eliminated through vaporization. Exemplary partition breaking solvents include butyl alcohol, amyl alcohol, hexyl alcohol, methyl isobutyl carbinol, iso-amyl alcohol, and secondary butyl alcohol. Other alcohols may be utilized such as heptanols and octonols. Emulsion breaking solvents other than alcohols such as mesityl oxide, isopropyl acetate, isobutyl acetate, isopropyl ether and methyl isobutyl ketone may also be employed.

The preferred partition breaking solvent is a butyl alcohol such as secondary butyl alcohol. Secondary butyl alcohol is preferentially oil soluble however, it also exhibits partial water solubility on the order of approximately 28%. Additionally, water is added to the reaction mixture with the partition breaking solvent or through line 58 before or after the partition breaking solvent and reaction mixture are intimately mixed in mixer 60.

In the exemplary embodiment of the present invention the preferred amount of partition breaking solvent added to the oil and sulfonic acid containing top layer of the reaction mixture is on the order of 10 to 180 parts per 100 parts of oil and sulfonic acid. Additionally, 5 to 50 parts of water are preferably added per 100 parts of oil and sulfonic acid. If desired, it is possible to increase the ratio of partition breaking solvent to oil and sulfonic acid while maintaining the water to solvent ratio. It should be noted that if water is not added to the reaction mixture the undesireable water soluble green sulfonic acid will remain in the mixture and cannot be separated effectively.

After mixing, the reaction mixture comprising unreacted oil, oil soluble sulfonic acids, hydrocarbon solvent and partition breaking solvent is transferred from mixer 60 via line 62 to settler 64. The mixture is allowed to stand for a sufficient period of time to effect a separation into three phases or layers within settler 64. Typically, the mixture is allowed to stand at room temperature for a period on the order of 15 minutes to several hours. The phases or layers formed upon separation comprise: a top phase of essentially all unreacted oil and a small amount of sulfonic acid; an intermediate or middle phase containing the desired oil soluble sulfonic acids as well as hydrocarbon solvent and partition breaking solvents; and a bottom, brine phase containing undesirable water soluble green sulfonic acids, sulfate and sulfite ions, hydrocarbon solvent and partition breaking solvent. Typical specific gravities for these three phases are as follows: Approximately 0.8–0.83 for the top phase; approximately 0.84 to 0.86 for the intermediate phase; and approximately 1.0 for the bottom phase.

The bottom brine phase is drawn from settler 64 by line 66 and may be neutralized with any base forming salt and water. After recovery of the hydrocarbon solvent and partition breaking solvent, the remaining brine solution may be discarded. It will be appreciated that the partition breaking solvent and hydrocarbon solvent preferably have boiling points which differ by a sufficient degree to enable them to be separately stripped from this solution. Boiling points varying on the order of 100 degrees F. are preferred for this purpose.

The top phase is drawn from settler 64 through line 68. This phase comprises essentially unreacted or white oil, hydrocarbon solvent, partition breaking solvent, and a slight amount of sulfonic acids. After stripping the solvent from the unreacted oil the remaining oil may be utilized as a lubricant or for other purposes. Typically, this unreacted oil fraction is relatively low in aromatic hydrocarbon because the overwhelming majority of aromatic hydrocarbon contained in the original feed stock has been converted to the desired oil soluble sulfonic acid.

The remaining middle phase containing the desired oil soluble sulfonic acids is removed from settler 64 by line 70. This middle phase also contains residual hydrocarbon solvents and partition breaking solvents. It will be appreciated at this point that the desired oil soluble sulfonic acid in this phase has been purified of undesirable ions and water soluble sulfonic acids through the previous steps. To this mixture is added a basic oxide or hydroxide of a polyvalent metal via line 72 before the resultant mixture is mixed in mixer 74, where the desired polyvalent metal sulfonates are formed, and conducted by line 76 to stripper 80. Polyvalent metals suitable for this purpose include the alkali-earth metals and more specifically include the preferred polyvalent metals calcium, barium, strontium, and magnesium. Sufficient polyvalent metal oxide or hydroxide is added to bring the pH of the reaction mixture to between 6 to 9 pH units.

In this manner the method of the present invention directly forms neutral oil soluble, water insoluble polyvalent metal mahogany sulfonates. Any excess or unreacted polyvalent metal oxide or hydroxide may be readily removed from the treated mixture through filtration, straining, or centrifugation. For example, in FIG. 1, the treated mixture is conducted from stripper 80 via line 82 to filter 86. The resulting filtrate is then conducted via line 88 to a second stripper 90 where the hydrocarbon solvent and partition breaking solvent is removed. The stripped solvents can be condensed and recycled in the process. The remaining stripped solution containing the neutral oil soluble polyvalent metal sulfonate is transferred to storage tank 94 via line 90. It should be noted that the polyvalent metal sulfonates produced through the method of the present invention can readily be recovered through filtration without the need for diatomaceous earth. Other recovery methods include straining or centrifugation.

The resultant neutralized oil soluble polyvalent metal sulfonates are commercially valuable products which can be utilized in compound lubricants or as feed stock in the manufacture of overbased or higher alkalinity value oil soluble polyvalent metal sulfonates. For example, as shown in FIG. 1, additional polyvalent metal oxide or hydroxide can be added to the polyvalent metal sulfonates by line 78 to stripper 80 where the mixture is heated. The mixture is then filtered and stripped of solvents. The stripped hydrocarbon solvent and partition breaking solvent can be recovered and recycled if desired.

EXAMPLE

The following example is provided as being illustrative of the principals of the present invention demonstrated on a smaller scale. 200 milliliters of refined natural feedstock in a flask was cooled in an ice bath. 26 milliliters of 26% oleum was slowly added to the feedstock with constant stirring while the temperature of the mixture was maintained below 130 degrees F. Thereafter, 4 milliliters of water were added to the mixture before 160 milliliters of V&MP (varnish and paint manufacturers) naphtha was added to the mixture. The contents of the flask were transferred to a separatory funnel and allowed to settle at room temperature for twenty-four hours. At that time three layers were observed to have formed. The top layer of approximately 330 milliliters in volume comprised oil soluble sulfonic acid, unreacted oil, V&MP naptha, and some water soluble sulfonic acids as well as sulfate and sulfite ions. The lower two layers of approximately 60 milliliters total volume comprised acid sludge, spent sulfuric acid, and water soluble sulfonic acid. These lower two layers were removed from the separatory funnel and discarded.

Three hundred millileters of the top layer were mixed with 245 milliliters of secondary butyl alcohol and 135 milliliters of water. The solution was mixed and transferred to a separatory funnel. Within fifteen minutes three layers were observed to form and were allowed to separate for one hour. The bottom layer comprising water soluble sulfonic acid, sulfate and sulfite ions, secondary butyl alcohol and V&MP naptha and water were drawn off and discarded.

The middle layer comprising oil soluble sulfonic acid, aqueous secondary butyl alcohol, and V&MP naptha was transferred to a beaker. The pH of the solution was measured at 0. Calcium hydroxide powder was slowly added to the solution with constant stirring until the pH of the solution was raised to approximately 7 to 9 pH units. The solution was filtered on Watman No. 1 filter paper and practically all solids (excess calcium hydroxide) were retained on the filter paper. The total filtration time was under 5 minutes. The pH of the filtrate was measured at 6.8 to 7.0 pH units. The secondary butyl alcohol and naphtha were stripped from this solution leaving oil soluble neutral calcium sulfonate. The remaining top layer was stripped of secondary butyl alcohol and naphtha to leave unreacted oil.

It will be appreciated that the embodiments of the present invention disclosed herein are illustrative of the principals of the present invention and other modifications and embodiments may be employed which are within the scope of the present invention. Thus, by way of example, but not of limitation the second mixer 26 and condenser 30 may be eliminated and the sulfonation process can be performed in one step. It will be appreciated however, that the illustrative embodiment of the present invention disclosed above is to be preferred. Accordingly, the present invention is not limited to that precisely as shown and described in the instant specification.

What is claimed is:

1. An improved method for the direct production and separation of oil soluble polyvalent metal sulfonates of aromatic hydrocarbon oils comprising the steps of:

sulfonating a natural hydrocarbon oil feed stock with a sulfonating agent to produce a mixture of oil soluble sulfonic acids, water soluble green sulfonic acids, unreacted acid, sulfate and sulfite ions, and unreacted oil;

adding from about 1 to 3 percent water to said mixture to quench the sulfonation reaction and to release said oil soluble sulfonic acids;

adding a hydrocarbon solvent to said mixture to promote the separation of said mixture into a top layer containing unreacted hydrocarbon oils, oil soluble sulfonic acids, hydrocarbon solvent, and small amounts of green sulfonic acid, sulfate and sulfite ions, and a bottom sludge layer containing the majority of said water soluble green sulfonic acids, unreacted acid, sulfate and sulfite ions;

removing said sludge layer;

adding a partition breaking solvent selected from the group consisting of alcohols having from 4 to 8 carbon atoms to said upper layer to promote the formation of an upper phase containing unreacted oil and trace amounts of oil soluble sulfonic acid, hydrocarbon solvent and partition breaking solvent, a middle phase containing oil soluble sulfonic acid, hydrocarbon solvent and partition breaking solvent, and a lower phase containing green sulfonic acids, unreacted acids, sulfate and sulfite ions;

separating said three phases;

treating said middle phase with oxides or hydroxides of a polyvalent metal to produce neutralized oil soluble polyvalent metal sulfonate; and recovering said oil soluble polyvalent metal sulfonate from said treated middle phase.

2. The method of claim 1 wherein said hydrocarbon feed stock has an aromatic content ranging from about 5 percent to 95 percent.

3. The method of claim 2 wherein said aromatic portion comprises compounds having molecular weights on the order of 200 to 1000.

4. The method of claim 1 wherein said hydrocarbon solvent is an aromatic compound having a boiling point on the order of 160° F. to 350° F.

5. The method of claim 4 wherein said solvent is selected from the group comprising benzene, toulene, xylene, and naphtha.

6. The method of claim 1 wherein said alcohol is aqueous secondary butyl alcohol.

7. The method of claim 1 wherein said polyvalent metal is an alkali-earth metal.

8. The method of claim 7 wherein said polyvalent metal is calcium, barium or magnesium.

9. The method of claim 1 wherein said neutralized oil soluble polyvalent metal sulfonate is recovered through stripping off the hydrocarbon solvent and partition breaking solvent from said treated middle phase.

10. An improved method for the recovery of oil soluble, polyvalent metal sulfonates of aromatic hydrocarbon oils from a sulfonated hydrocarbon feed stock containing a mixture of oil soluble sulfonic acids, green sulfonic acids, unreacted acid, sulfate and sulfite ions, and unreacted oil comprising the steps of:

adding a hydrocarbon solvent to said treated hydrocarbon feed stock to promote the separation of said treated hydrocarbon feed stock into a top layer containing unreacted hydrocarbon oils, oil soluble sulfonic acids, hydrocarbon solvent, and small amounts of green sulfonic acid, sulfate and sulfite ions, and a bottom sludge layer containing the majority of green sulfonic acids, unreacted acid, sulfate and sulfite ions;

treating said top layer with a partition breaking solvent selected from the group consisting of alcohols having from 4 to 8 carbon atoms to promote the formation of an upper phase containing unreacted oil and trace amounts of sulfonic acid, a middle phase containing oil soluble sulfonic acid, hydrocarbon solvent and partition breaking solvent, and a lower phase containing green sulfonic acids, unreacted acids, sulfate and sulfite ions;

treating said middle phase with oxides or hydroxides of a polyvalent metal to produce neutralized oil soluble polyvalent metal sulfonates; and recovering said oil soluble polyvalent metal sulfonate from said treated middle phase.

11. The method of claim 10 wherein said hydrocarbon solvent is an aromatic compound having a boiling point on the order of 160° F. to 350° F.

12. The method of claim 11 wherein said solvent is selected from the group comprising benzene, toulene, xylene, and naphtha.

13. The method of claim 10 wherein said alcohol is aqueous secondary butyl alcohol.

14. The method of claim 10 wherein said polyvalent metal ion is an alkali-earth metal.

15. The method of claim 14 wherein said polyvalent metal is calcium, barium or magnesium.

16. The method of claim 10 wherein said neutralized oil soluble polyvalent metal sulfonate is recovered through stripping off the hydrocarbon solvent and partition breaking solvent from said treated middle phase.

* * * * *